US009175257B2

(12) United States Patent
Colavizza et al.

(10) Patent No.: US 9,175,257 B2
(45) Date of Patent: Nov. 3, 2015

(54) YEAST STRAINS FOR PRODUCING ALCOHOL

(75) Inventors: Didier Colavizza, Roubaix (FR); Renaud Toussaint, Gondecourt (FR)

(73) Assignee: LESAFFRE ET COMPAGNIE, Paris (FR)

( * ) Notice: Subject to any disclaimer, the term of this patent is extended or adjusted under 35 U.S.C. 154(b) by 39 days.

(21) Appl. No.: 13/062,995

(22) PCT Filed: Sep. 10, 2009

(86) PCT No.: PCT/FR2009/001080
§ 371 (c)(1),
(2), (4) Date: Mar. 9, 2011

(87) PCT Pub. No.: WO2010/031916
PCT Pub. Date: Mar. 25, 2010

(65) Prior Publication Data
US 2011/0165612 A1    Jul. 7, 2011

(30) Foreign Application Priority Data

Sep. 16, 2008 (FR) ...................................... 08 05056

(51) Int. Cl.
*A01N 1/02* (2006.01)
*C12N 1/18* (2006.01)
*C12R 1/865* (2006.01)

(52) U.S. Cl.
CPC .. *C12N 1/18* (2013.01); *C12R 1/865* (2013.01)

(58) Field of Classification Search
CPC .......... A61K 36/06; C12N 15/80; C12N 1/16; C12N 1/18; C12P 1/02; C12R 1/85; C12R 1/865
USPC .......................................................... 435/29
See application file for complete search history.

(56) References Cited

FOREIGN PATENT DOCUMENTS

WO    WO 98/31784       7/1998
WO    WO9831784    *   7/1998    ............... C12N 1/16

OTHER PUBLICATIONS

Rainieri et al. Oenological properties of an interspecific Saccharomyces hybrid. S Afr J Enol Vitic. 1999:20(2);47-52.*
Romano et al. Improvement of a wine Saccharomyces cerevisiae strain by a breeding program. Applied and Environmental microbiology. 1985;50:1064-1067.*
Verma et al. Use of yeast cell recycling for rapid ethanol production from molasses. J. Ferment. Technol. 1983;61(5):527-531.*
Bakker et al. Fermentation modeling cellulosic biomass conversion. Fluent Incorporated. 2004;1-32.*
Rainieri et al. Oenological properties of an interspecific Saccharomyces hybrid. S. Afr. J. Enol. Vitic. 1999;20(2):47-52.*
Rainieri et al. Characterisation of thermotolerant Saccharomyces cerevisiae hybrids. Biotechnology Letters. 1998;20(6):543-547.*
Miklos et al. Breeding of a distiller's yeast by hybridization with a wine yeast. Appl Microbiol Biotechnol. 1991;35:638-642.*
de Winde J.H. Functional genetics of industrial yeasts. Springer. 2003;1-367.*
PCT International Search Report received in PCT/FR2009/001080.
Blasco et al., "Genetic stabilization of Saccharomyces cerevisiae oenological strains by using benomyl" *International Microbiology*, vol. 11, pp. 127-132 (2008).
Carro et al., "Genetic analysis of the karyotype instability in natural wine yeast strains" *Yeast*, vol. 18, pp. 1457-1470 (2001).
Marullo et al. "Inheritable nature of enological quantitative traits is demonstrated by meiotic segregation of industrial wine yeast strains" *FEMS Yeast Research*, vol. 4, pp. 711-719 (2004).
Miklos et al., "Breeding of a distiller's yeast by hybridization with a wine yeast" *Applied Microbiology Biotechnology*, vol. 35, pp. 638-642 (1991).
Romano et al., "Improvement of Wine Saccharomyces cerevisiae strain by a breeding program" *Applied and Environmental Microbiology*, vol. 50, pp. 1064-1067 (1985).
Sipiczki et al., "Genetic segregation of natural Saccharomyces cerevisiae strains derived from spontaneous fermentation of Aglianico wine" *Journal of Applied Microbiology*, vol. 96, pp. 1169-1175 (2004).
Jacques et al., "Yeast Mutations", *The Alcohol Textbook*, 4th Edition, Understanding yeast fundamentals, p. 113 (2003).
Verma et al., "Use of Yeast Cell Recycling for Rapid Ethanol Production from Molasses", *Ferment. Technol.*, vol. 61, No. 5, pp. 527-531 (1983).
Walker et al., "Yeast inoculum development", *Yeast Physiology and Biotechnology* Yeast Growth, p. 143 (1998).
Powell et al. "Long Term Serial Repitching and the Genetic and Phenotypic Stability of Brewer's Yeast", *Journal of the Institute of Brewing*, vol. 113, No. 1, pp. 67-74 (2007).

* cited by examiner

*Primary Examiner* — Ruth Davis
*Assistant Examiner* — Lynn Y Fan
(74) *Attorney, Agent, or Firm* — Vedder Price P.C.; Thomas J. Kowalski; Deborah L. Lu

(57) ABSTRACT

The present invention relates to novel stable yeast strains, to a novel method for obtaining such strains, and to a novel method for evaluating the stability of a yeast strain. The present invention also relates to the yeasts obtained from these novel stable yeast strains, and to the use thereof for producing alcohol.

3 Claims, No Drawings

YEAST STRAINS FOR PRODUCING ALCOHOL

TECHNICAL FIELD

The present invention relates to novel yeast strains and yeasts stemming from these novel strains intended for producing alcohol, and also to a method for obtaining such strains.

TECHNICAL BACKGROUND

Yeasts frequently undergo mutations during their multiplication and during their use in fermentation, in particular on the industrial scale. However, these yeasts generally retain a normal phenotype because the mutations are often recessive mutations and the industrial strains are normally aneuploid or polyploid (The Alcohol Textbook, Ed Jacques (2003)).

Yeast recycling is often used in alcoholic fermentation. Yeast recycling consists of several successive uses of the yeasts, without re-starting from the initial yeasts or initial strain. Thus, all or part of the yeasts stemming from a fermentation i are used for a subsequent fermentation i+1; then all or part of the yeasts stemming from the fermentation i+1 are used for a fermentation i+2, and so on.

Yeast recycling, sometimes called "serial subculture" in the literature, is a technique which exposes the yeast to a large number of stresses that can lead to mutations in its genetic inheritance and genetic drifts.

In their work, Powell and Diacetis (2007, J. Inst. Brew. 1131(1), 67-74) study the impact of the recycling of brewers' yeasts on their phenotype. At the end of each fermentation, a part of the yeast biomass is taken in order to carry out the subsequent fermentation. Powell and Diacetis observed no modification to the fermentation characteristics of the yeasts during successive subcultures, over approximately 135 generations.

Verma et al. (1983) studied, moreover, the advantage of recycling various *Saccharomyces cerevisiae* yeasts in the context of ethanol production. After each alcoholic fermentation, the yeasts are subcultured for the purpose of a further fermentation, and the amount of alcohol produced at the end of each fermentation is measured. The authors demonstrated several yeast strains capable of undergoing 6 to 10 successive subcultures without their alcohol production being substantially modified.

Thus, in the literature, yeast stability in terms of alcohol production has therefore been studied in the context of yeast recycling in alcoholic fermentation.

When it is multiplied in a conventional industrial process, the most effective yeast, in terms of alcohol production, known to the applicant company sometimes shows, however, considerable decreases in the amount of alcohol produced. However, industrial-scale yeast multiplication starting from a yeast strain should result in a strain of reliable quality. The term "reliable quality" is herein intended to mean that the amount of alcohol produced by the yeast, in a given alcohol fermentation scheme, is relatively constant.

Moreover, the market for yeast intended for alcohol production is always demanding yeasts that are more effective in terms of amount of alcohol produced.

There is therefore a real need to provide novel yeast strains which give yeasts of reliable quality and which are preferably effective in terms of amount of alcohol produced.

SUMMARY OF THE INVENTION

A first subject of the invention is to provide novel stable yeast strains.

A subject of the present invention is thus a stable *Saccharomyces cerevisiae* strain chosen from the strain deposited with the CNCM under number I-4073, the strain deposited with the CNCM under number I-4074 or the strain deposited with the CNCM under number I-4075.

A second subject of the invention is to provide a novel method for obtaining stable yeast strains, said method comprising the steps of:
  crossing an unstable *Saccharomyces* strain with itself or with another *Saccharomyces* strain, so as to obtain at least one hybrid,
  culturing at least one hybrid, so as to obtain a yeast population R0,
  carrying out n successive subcultures of the yeast population R0, n being an integer greater than or equal to 6, so as to obtain a yeast population Rn,
  measuring the alcohol production of said population R0 and measuring the alcohol production of said population Rn,
  selecting at least one hybrid for which the alcohol production of the population Rn is greater than or equal to 95% of that of the population R0, so as to obtain stable yeast strains.

A subject of the present invention is particularly a method for obtaining stable yeast strains as defined above, comprising an additional step of selecting at least one hybrid for which the alcohol production of the population R0 is greater than or equal to 95% of that of a population R0 of the strain deposited with the CNCM on Sep. 4, 2008, under number I-4072.

A subject of the present invention is also a method for obtaining stable yeast strains as defined above, comprising an additional step of selecting at least one hybrid which has a biomass yield greater than or equal to 90% of the biomass yield of the I-4072 strain.

A subject of the present invention is also a method for obtaining stable yeast strains as defined above, characterized in that the step of crossing yeast strains comprises the following steps:
  sporulating said unstable *Saccharomyces* strain and, optionally, said other *Saccharomyces* strain, so as to obtain segregants,
  culturing each segregant, so as to obtain a population R0 for each segregant,
  carrying out m successive subcultures of each segregant, so as to obtain a population Rm of each segregant, m being an integer greater than or equal to 6,
  measuring the alcohol production of the population R0 and measuring the alcohol production of the population Rm of each segregant,
  selecting the segregants for which:
    the alcohol production of the population Rm is greater than or equal to 70% of that of the population R0 of said segregant, and
    the alcohol production of the population Rm is greater than or equal to 85% of that of the population R0 of the I-4072 strain, so as to obtain effective and stable segregants, and
  crossing effective, stable segregants stemming from said unstable strain with effective and stable segregants of opposite sign stemming from said unstable strain or from said other strain, so as to obtain at least one hybrid.

A subject of the present invention is particularly a method for obtaining stable yeast strains as defined above, in which said unstable yeast strain is the I-4072 strain.

The subject of the present invention is also a method for obtaining stable yeast strains as defined above, in which said other strain is chosen from the I-4071 strain, the I-4073 strain, the I-4074 strain or the I-4075 strain.

A third subject of the invention relates to a yeast strain that can be obtained by means of the method for obtaining stable yeast strains as defined above.

A fourth subject of the invention is the provision of a *Saccharomyces cerevisiae* strain derived from a strain as defined above, characterized in that:
- the alcohol production of a population $R_n$ of said derived strain is greater than or equal to 95% of the alcohol production of a population $R_0$ of said derived strain, and/or
- the alcohol production of a population $R_0$ of said derived strain is greater than or equal to 95% of the alcohol production of a population $R_0$ of the strain deposited with the CNCM under number I-4072,
- the population $R_n$ stemming from n successive subcultures of the population $R_0$, n being an integer greater than or equal to 6.

A fifth subject of the invention is the provision of a novel method for evaluating the stability of a yeast strain, comprising the steps of:
- culturing said strain, so as to obtain a yeast population $R_0$,
- carrying out n successive subcultures of the yeast population $R_0$, n being an integer greater than or equal to 6, so as to obtain a yeast population $R_n$,
- measuring the alcohol production of said population $R_0$ and measuring the alcohol production of said population $R_n$,
- describing said strain as "stable" if the alcohol production of the population $R_n$ is greater than or equal to 95% of the alcohol production of the population $R_0$.

A sixth subject of the invention relates to a yeast obtained by culturing a yeast strain as defined above.

A subject of the present invention is particularly a yeast as defined above, characterized in that the alcohol production thereof is greater than or equal to 95% of the alcohol production of a yeast stemming from the I-4072 strain.

A subject of the present invention is also a yeast as defined above, characterized in that it is in the form of cream yeast, pressed yeast, dry yeast or deep-frozen yeast.

A seventh subject of the invention relates to the use of a yeast as defined above, for producing alcohol.

DETAILED DESCRIPTION OF THE INVENTION

A subject of the present invention is to provide novel *Saccharomyces cerevisiae* strains and of novel yeasts stemming from these strains intended for producing alcohol, said yeasts being of reliable quality and preferably being effective in terms of amount of alcohol produced.

In order to obtain a yeast of reliable quality, it is necessary to have a stable yeast strain.

A stable yeast strain denotes herein a strain which gives yeasts of which the alcohol production is relatively stable over the generations.

In order to obtain a yeast that is effective, in terms of amount of alcohol produced, it is necessary to have a yeast strain which is effective in terms of amount of alcohol produced.

The expressions "alcohol production", "ethanol production", "amount of alcohol produced" and "amount of ethanol produced" are synonyms herein.

Any strain which does not correspond to the definition of a stable strain is described as an unstable strain.

Surprisingly and unexpectedly, the applicant company has demonstrated that, during the industrial-scale multiplication of yeasts, starting from the I-4072 strain, variants appear, the alcohol production of which is low. After a certain number of generations, the increasing proportion of variants results in a considerable decrease in the amount of alcohol produced.

Now, this problem of stability in terms of alcohol production, which appears during yeast multiplication, has never been demonstrated in the literature.

This is because the prior art documents tackle the problem of strain stability only in the context of yeast recycling between several alcoholic fermentations.

There was therefore a need to provide a method for distinguishing stable yeast strains from unstable yeast strains.

In order to be able to verify that a yeast strain is stable, in terms of alcohol production, the applicant company has developed a novel method for evaluating the stable nature of a strain.

This original method for evaluating the stability of a yeast strain is based on carrying out several successive subcultures starting from the strain to be evaluated, in order to obtain a multiplication of the yeasts which mimics that obtained during an industrial-scale multiplication.

The method for evaluating the stability of a yeast strain according to the invention comprises an original combination of two steps:
- a first step consisting of several successive subcultures starting from the initial strain, and
- a second step of comparing the alcohol production of the yeast population obtained at the end of the successive subcultures with that of the initial strain to be evaluated.

Thus, if the alcohol production of the yeast population obtained at the end of the subcultures has not substantially decreased compared with the alcohol production of the initial strain to be evaluated, the strain is described as a stable strain.

The first step of successive subcultures preferably results in a number of yeast generations greater than or equal to that obtained at the end of an industrial-scale yeast multiplication.

The method for evaluating the stability of a strain according to the invention has many advantages. It is in particular a rapid method which gives reliable results and which can be implemented in the laboratory.

The implementation of the method according to the invention provides a considerable advantage for a manufacturer, equally in terms of time, cost and quality of its products, by avoiding in particular carrying out several industrial multiplications of an unstable strain.

A subject of the present invention is thus a method for evaluating the stability of a yeast strain, comprising the steps of:
- culturing said strain, so as to obtain a yeast population $R_0$,
- carrying out n successive subcultures of the yeast population $R_0$, n being an integer greater than or equal to 6, so as to obtain a yeast population $R_n$,
- measuring the alcohol production of said population $R_0$ and measuring the alcohol production of said population $R_n$,
- describing said strain as "stable" if the alcohol production of the population $R_n$ is greater than or equal to 95% of the alcohol production of the population $R_0$.

The expression "yeast strain" denotes a relatively homogeneous population of yeast cells.

A yeast strain is obtained from the isolation of a clone, a clone being a population of cells obtained from a single yeast cell.

The strain to be evaluated is in particular a strain intended for the production of yeasts used in distilling and/or in wine-making and/or in brewing and/or for the production of fermented beverages.

The strain to be evaluated is preferably a *Saccharomyces* strain, in particular a *Saccharomyces cerevisiae* strain.

The method according to the invention is not limited to evaluating the stability of yeast strains. It can also be applied to yeasts.

The term "yeasts" denotes yeasts obtained by culturing starting from a yeast strain.

The culturing of the yeast strain to be evaluated is carried out in a culture medium suitable for the growth of the yeast strain.

Those skilled in the art are capable of determining the composition of a medium suitable for a given yeast strain.

The culturing of the yeast strain can be carried out in a liquid medium or on an agar medium.

The culturing of the yeast strain is preferably carried out on an agar medium.

The culturing of the yeast strain is generally carried out at a temperature of from 25° C. to 35° C., preferably from 28° C. to 32° C.

The culturing of the yeast strain is generally carried out at a temperature of 30° C.

The culturing of the yeast strain to be evaluated results in a yeast population called R0.

Next, n successive subcultures are carried out starting from the population R0. This means that all or part of the culture corresponding to the yeast population R0 is inoculated for the following culture which results in a yeast population G1; then all or part of the culture corresponding to the yeast population G1 is inoculated for the following culture which results in a yeast population G2, and so on, until the culture which results in a yeast population Rn.

The n successive subcultures are preferably carried out at regular time intervals.

Preferably, the n successive subcultures are daily subcultures.

In one preferred embodiment, the n subcultures are carried out in the same medium and/or at the same temperature and/or with the same amount of inoculated biomass.

The biomass is defined as the mass of a yeast population.

For example, during each subculture, a biomass corresponding to a dry mass of 0.05 mg of yeasts is inoculated, preferably at the surface of an agar medium.

If required, the biomass harvested at the end of a subculture can be stored at 4° C. for several days, for example 1 to 2 days, before being inoculated for the following subculture.

The successive subcultures can be carried out as indicated in example 1.

The method for evaluating the stability of a strain comprises a number of subcultures greater than or equal to 6, preferably greater than or equal to 10, more preferably greater than or equal to 12, and even more preferably greater than or equal to 14.

In one preferred embodiment, the method of evaluation according to the invention comprises 12 successive subcultures.

It is possible to determine the number of yeast generations obtained after n successive subcultures by calculating the number of generations obtained between each of the n subcultures (cf. "Yeast Physiology and Biotechnology", 1998, Graeme M. Walker, published by Wiley, p. 143).

The number of generations $n_g$ between two successive subcultures i and i+1 is obtained by:
  measuring the biomass $(X_i)$ inoculated for the $i^{th}$ subculture and the biomass $(X_{i+1})$ harvested at the end of the $i^{th}$ subculture, then
  applying the following formula:

$$n_g = 3.3 \log(X_{i+1}/X_i)$$

The biomass X can be expressed as number of yeast cells or as weight of dry matter.

The number of yeast cells is determined by conventional methods well known to those skilled in the art, such as counting under a microscope or flow cytometry.

The weight of dry matter is determined by conventional methods well known to those skilled in the art.

The total number of generations obtained after n successive subcultures corresponds to the addition of the number of generations obtained between each subculture.

By way of example, the number of generations obtained over 12 successive daily subcultures is of the order of approximately 60 generations.

A number of generations greater than or equal to that obtained at the end of an industrial-scale yeast multiplication, which is generally of the order of approximately 50 to approximately 60 generations, is thus obtained.

This original method for evaluating the stability of a yeast strain thus makes it possible to obtain, on the laboratory scale, a number of generations greater than or equal to that obtained during an industrial multiplication of yeasts.

Preferably, the conditions of the method for evaluating the stability of a strain make it possible to obtain at least 30 generations, preferably at least 40 generations, more preferably at least 50 generations, and even more preferably at least 60 generations.

The alcohol production is measured by any suitable means known to those skilled in the art. It may be a direct measurement of the ethanol produced or an indirect measurement via a parameter correlated with the alcohol production.

For example, the alcohol production can be measured by chromatography, in particular by HPLC (High Performance Liquid Chromatography), an enzymatic kit (for example, the Boehringer kit for assaying ethanol), or an assay with potassium dichromate.

The alcohol production is preferably measured in an alcoholic fermentation test as described in example 1.

In such a test, the yeast strain is multiplied in a liquid medium, preferably in two steps: a preculture step followed by a culture step. The alcoholic fermentation is then carried out, for example starting from 1 g of yeast dry matter, at 35° C., under anaerobic conditions, preferably under stirring.

The substrate for the alcoholic fermentation is preferably in the form of sucrose initially present in the culture medium, for example at a concentration of 240 g/L.

The alcohol production measurement is generally expressed as percentage by volume.

The curve of alcoholic fermentation representing the amount of alcohol produced as a function of time generally comprises three phases:
  a lag phase, during which there is no ethanol production,
  an exponential phase, and
  a plateau phase, this phase corresponding to the maximum amount of ethanol produced during this alcoholic fermentation.

The alcohol production can be measured at a time (t) which is at the end of the exponential phase or during the plateau phase.

The alcohol production can be measured at $t_1$ and/or $t_2$, as defined below.

The measurement at $t_1$ is at the end of the exponential phase, at a time greater than or equal to that which corresponds to 95% of the maximum amount of alcohol produced.

This measurement of $t_1$ makes it possible in particular to assess the alcohol production kinetics.

The measurement at $t_2$ is during the plateau phase, i.e. when the alcoholic fermentation is finished.

The end of the alcoholic fermentation corresponds to the time at which there is no more residual sugar, in the medium, that can be fermented by the yeast.

This measurement at $t_2$ also makes it possible to assess the maximum volume of alcohol produced.

By way of example, under the conditions defined in the examples, the alcohol production can be measured at $t_1=48$ h and/or at $t_2=72$ h.

The last step in the method for evaluating the stability of a strain consists in describing as a stable strain a strain of which the alcohol production of its population Rn is greater than or equal to 95% of the alcohol production of its population R0.

The strain is in particular described as a stable strain when the alcohol production of the population Rn of said strain is greater than or equal to 97%, preferably greater than or equal to 99%, of the alcohol production of its population R0.

A strain is described as an unstable strain when the alcohol production of the population Rn of said strain is less than 95% of the alcohol production of its population R0.

The implementation of the method for evaluating the stability of a strain according to the invention makes it possible to confirm that the I-4072 strain is an unstable strain: the alcohol production of its population R12 is equal to 49% at $t_1=48$ h and to 46.9% at $t_2=72$ h, of the alcohol production of its population R0 (see example 1).

Moreover, the applicant company has also developed a novel original method for obtaining stable yeast strains.

The implementation of this method has in particular made it possible to obtain the three novel *Saccharomyces cerevisiae* strains deposited on Sep. 4, 2008, pursuant to the Treaty of Budapest, with the CNCM (Collection Nationale de Cultures de Microorganismes [National collection of microorganism cultures], Institut Pasteur, 25 rue du Docteur Roux, F-75724 Paris Cedex 15, France) under accession numbers I-4073, I-4074 and I-4075. Additionally, the I-4072 *Saccharomyces cerevisiae* reference strain was deposited on Sep. 4, 2008 with the CNCM under accession number I-4072.

A subject of the present invention is thus a *Saccharomyces cerevisiae* strain chosen from the strain deposited with the CNCM under number I-4073, the strain deposited with the CNCM under number I-4074 or the strain deposited with the CNCM under number I-4075.

These three yeast strains are both stable and effective.

The stability of these yeast strains is reflected by the small difference in the amount of alcohol produced, after n successive subcultures, compared with the initial strain.

The evaluation of the stability of the strains according to the invention can be carried out as described above in the method for evaluating the stability of a strain.

The stability of the three strains according to the invention is thus reflected by a decrease in the alcohol production of less than 3% after n subcultures, whereas an unstable strain such as the I-4072 reference strain shows a decrease in alcohol production of greater than 50% (see example 1).

The effectiveness of the yeast strains according to the invention is reflected by an alcohol production of said strains similar to that of the I-4072 reference strain.

The effectiveness of the three yeast strains according to the invention is thus reflected by an alcohol production of said strains of greater than or equal to 95% of that of the reference strain.

The *Saccharomyces cerevisiae* strain deposited on Sep. 4, 2008 with the CNCM under number I-4075 has in particular the following characteristics:
  the alcohol production of the population R12 of said strain is greater than or equal to 97% of the alcohol production of the population R0 of said strain, the population R12 stemming from 12 successive daily subcultures of the population R0, and
  the alcohol production of the population R0 of said strain is greater than or equal to 99% of the alcohol production of the population R0 of the strain deposited with the CNCM under number I-4072 (during a measurement at 48 h).

The *Saccharomyces cerevisiae* strain deposited on Sep. 4, 2008 with the CNCM under number I-4073 has in particular the following characteristics:
  the alcohol production of the population R12 of said strain is greater than or equal to 98% of the alcohol production of the population R0 of said strain, the population R12 stemming from 12 successive daily subcultures of the population R0, and
  the alcohol production of the population R0 of said strain is greater than or equal to 99% of the alcohol production of the population R0 of the strain deposited with the CNCM under number I-4072.

The *Saccharomyces cerevisiae* strain deposited on Sep. 4, 2008 with the CNCM under number I-4074 has in particular the following characteristics:
  the alcohol production of the population R12 of said strain is greater than or equal to 98% of the alcohol production of the population R0 of said strain, the population R12 stemming from 12 successive daily subcultures of the population R0, and
  the alcohol production of the population R0 of said strain is greater than or equal to 99% of the alcohol production of the population R0 of the strain deposited with the CNCM under number I-4072.

A subject of the present invention is therefore the three strains described above and all of the strains belonging to the same family, in particular all the derived strains which share the same properties as these three strains.

Moreover, a subject of the present invention is a novel original method for obtaining stable yeast strains, based on selecting novel strains which correspond to the description of stable strain in the method for evaluating the stability of a strain as defined above.

Said selection is carried out on novel yeast strains obtained by conventional techniques.

A conventional technique consists of a step of sporulating yeasts to obtain segregants, followed by a step of crossing the segregants so as to obtain hybrids. The hybrids constitute the yeast strains which are subsequently selected on the criterion of stability.

A subject of the present invention is thus a method for obtaining stable yeast strains, said method comprising the steps of:
  crossing an unstable *Saccharomyces* strain with itself or with another *Saccharomyces* strain, so as to obtain at least one hybrid,
  culturing at least one hybrid, so as to obtain a yeast population R0, carrying out n successive subcultures of the yeast population R0, n being an integer greater than or equal to 6, so as to obtain a yeast population Rn, measuring the alcohol production of said population R0 and measuring the alcohol production of said population Rn, selecting at least one hybrid for which the alcohol production of the population Rn is greater than or equal to 95% of that of the population R0, so as to obtain stable yeast strains.

The crossing step is carried out according to conventional techniques, such as those taught in chapter 7 "Sporulation and Hybridization of Yeast" by R. R. Fowell, from the reference manual "The Yeasts", Volume 1, edited by A. H. Rose and J. S. Harrison, 1969-Academic Press.

The steps of culturing at least one hybrid, carrying out n successive subcultures and measuring the alcohol production are similar to those of the method for evaluating the stability of a strain.

The conditions for carrying out these steps are therefore the same as those described above in the context of the method for evaluating the stability of a strain.

The last step in the method for obtaining stable yeast strains consists in selecting at least one hybrid for which the alcohol production of the population Rn is greater than or equal to 95% of that of the population R0, such a hybrid constituting a stable yeast strain.

Preferably, the last step in the method for obtaining stable yeast strains consists in selecting at least one hybrid for which the alcohol production of the population Rn is greater than or equal to 97% of that of the population R0.

A subject of the present invention is particularly a method for obtaining stable yeast strains as defined above, in which the last selection step comprises selecting at least one hybrid for which the alcohol production of the population Rn is greater than or equal to 97% of that of the population R0, preferably greater than or equal to 99% of that of the population R0.

The stable strains according to the invention, the unstable strain used in the crossing step and said other *Saccharomyces* strain used in the crossing step may be homothallic or heterothallic strains.

In one preferred embodiment of the invention, the stable strains according to the invention, the unstable strain used in the crossing step and said other *Saccharomyces* strain used in the crossing step are heterothallic strains.

A subject of the present invention is also a method for obtaining yeast strains which are both stable and effective in terms of alcohol production.

A subject of the present invention is thus a method for obtaining stable yeast strains as defined above, comprising an additional step of selecting at least one hybrid for which the alcohol production of the population R0 is greater than or equal to 95% of that of the population R0 of the I-4072 strain.

This additional step of selecting on the basis of effectiveness in terms of alcohol production is carried out before or after the step of selecting the hybrids on the criterion of stability.

A subject of the present invention is particularly a method for obtaining stable yeast strains as defined above, in which the additional selection step comprises selecting at least one hybrid for which the alcohol production of the population R0 is greater than or equal to 97%, preferably greater than or equal to 99% of that of the population R0 of the I-4072 strain.

A subject of the present invention is also a method for obtaining yeast strains which are both stable and effective in terms of alcohol production and which have a good biomass yield.

The term "yield" or "biomass yield" or "biomass production yield" denotes herein the ratio of the mass of yeast produced to the mass of sugar used during the multiplication of the yeasts.

A subject of the present invention is thus a method for obtaining stable yeast strains as defined above, comprising an additional step of selecting at least one hybrid which has a biomass yield of greater than or equal to 90% of the biomass yield of the I-4072 strain, preferably greater than or equal to 95%, and more preferably greater than or equal to 98%.

This additional step of selecting on the basis of the biomass yield is carried out before or after the step of selecting the hybrids on the criterion of stability and, if necessary, before or after the step of selecting on the basis of effectiveness in terms of alcohol production.

Advantageously, the biomass yield of the strains according to the invention is greater than or equal to 90%, preferably greater than or equal to 95%, more preferably greater than or equal to 98% of the biomass yield obtained with the I-4072 strain.

In one preferred embodiment, the method for obtaining stable yeast strains comprises a preselection at the segregant level.

The segregants obtained after sporulation of the yeasts are then selected on the basis of stability and effectiveness.

A subject of the present invention is thus a method for obtaining novel stable yeast strains as defined above, characterized in that the step of crossing yeast strains comprises the following steps:

sporulating said unstable *Saccharomyces* strain and, optionally, said other *Saccharomyces* strain, so as to obtain segregants, culturing each segregant, so as to obtain a population R0 for each segregant, carrying out m successive subcultures of each segregant, so as to obtain a population Rm of each segregant, m being an integer greater than or equal to 6, measuring the alcohol production of the population R0 and measuring the alcohol production of the population Rm of each segregant, selecting the segregants for which:
   the alcohol production of the population Rm is greater than or equal to 70% of that of the population R0 of said segregant, and
   the alcohol production of the population Rm is greater than or equal to 85% of that of a population R0 of the I-4072 strain, so as to obtain effective, stable segregants, and crossing effective, stable segregants stemming from said unstable strain with effective, stable segregants of opposite sign stemming from said unstable strain or from said other strain, so as to obtain at least one hybrid.

The steps of culturing each segregant, of carrying out m successive subcultures and of measuring the alcohol production are similar to those of the method for evaluating the stability of a strain.

The conditions for implementing these steps are therefore the same as those described above in the context of the method for evaluating the stability of a strain.

The step of selecting the segregants on the basis of stability and effectiveness in terms of alcohol production results in the obtaining of effective, stable segregants, on the basis of criteria that are less selective than those applied to the hybrids or to the yeast strains.

In one particular embodiment of the method for obtaining stable yeast strains, said unstable yeast strain is the I-4072 strain.

In one particular embodiment of the method for obtaining stable yeast strains, said other yeast strain is chosen from the I-4071 strain, the I-4073 strain, the I-4074 strain or the I-4075 strain.

Said other yeast strain is preferably a *Saccharomyces cerevisiae* strain.

A subject of the present invention is also a yeast strain that can be obtained by means of the method for obtaining strains as defined above.

A subject of the present invention is in particular a yeast strain obtained by means of the method for obtaining strains as defined above.

A subject of the present invention is also all the strains derived from the stable yeast strains according to the invention which share the same properties.

The expression "derived strain" denotes a strain derived by any transformation, for instance one or more crosses and/or one or more mutations and/or one or more genetic transformations.

A strain derived by crossing can be obtained by crossing a strain according to the invention with the same strain, or another strain according to the invention, or any other strain.

A strain derived by mutation can be a strain which has undergone at least one spontaneous mutation in its genome or at least one induced mutation, for example induced by mutagenesis.

The mutation(s) of the derived strain is (are) silent or not.

The term "mutagenesis" denotes both conventional mutagenesis obtained by radiation or by mutagenic chemical agents and insertional mutagenesis by transposition or by integration of an exogenous DNA fragment.

Mutagenesis by radiation comprises the use of UV-, X- or gamma-radiation.

The mutagenic chemical agents are, for example, EMS (ethyl methane sulfonate), EES (ethyl ethane sulfonate), nitrosoguanidine, nitrous acid, aflatoxin B1, hydroxylamine, 5-bromouracil, 2-aminopurine, proflavine and acridine orange.

A strain derived by genetic transformation is a strain into which an exogeneous DNA has been introduced.

Said exogenous DNA can be provided by a plasmid.

Said exogenous DNA is preferably integrated into the genome of the yeast.

A subject of the present invention is thus a *Saccharomyces cerevisiae* strain derived from a stable yeast strain as defined above, characterized in that:
the alcohol production of a population $R_n$ of said derived strain is greater than or equal to 95% of the alcohol production of a population $R_0$ of said derived strain, and/or
the alcohol production of a population $R_0$ of said derived strain is greater than or equal to 95% of the alcohol production of a population $R_0$ of the strain deposited with the CNCM under number I-4072,
the population $R_n$ stemming from n successive subcultures of the population $R_0$, n being an integer greater than or equal to 6.

The number of subcultures is preferably equal to 12 and they are preferably daily subcultures.

A subject of the present invention is particularly a *Saccharomyces cerevisiae* strain derived from a strain as defined above, characterized in that:
the alcohol production of a population $R_n$ of said derived strain is greater than or equal to 95% of the alcohol production of a population $R_0$ of said derived strain, preferably greater than or equal to 97%, more preferably greater than or equal to 99%, and
the alcohol production of a population $R_0$ of said derived strain is greater than or equal to 95% of the alcohol production of a population $R_0$ of the strain deposited with the CNCM under number I-4072, preferably greater than or equal to 97%, more preferably greater than or equal to 99%,
the population $R_n$ stemming from n successive subcultures of the population $R_0$, n being an integer greater than or equal to 6.

A subject of the invention is also a method for transforming a stable yeast strain, so as to obtain a derived strain as defined above, said method of transformation comprising a step of transforming said strain by means of at least one cross and/or at least one mutation and/or at least one genetic transformation.

A subject of the present invention is also a yeast obtained by culturing a yeast strain as defined above.

The yeasts are produced starting from stable yeast strains according to the invention, in particular as described in the reference manual "Yeast Technology" $2^{nd}$ edition, 1991, G. Reed and T. W. Nagodawithana, published by Van Nostrand Reinhold, ISBN 0-442-31892-8.

The industrial-scale multiplication of yeasts comprises, in general, at least the first two steps and the last step of the set of the following steps:
multiplying a yeast strain in several stages, first under semi-anaerobic conditions, and then under aerobic conditions,
separating the yeast thus produced, from its culture medium, by centrifugation, so as to obtain a liquid cream yeast containing approximately between 12% and 25% of dry matter, or even a higher amount of dry matter if the cream yeast is mixed with osmolyte products,
filtering the resulting liquid cream yeast, in general on a rotary filter under vacuum, so as to obtain a dehydrated fresh yeast containing from 26% to 35% of dry matter,
mixing said dehydrated fresh yeast, so as to obtain a homogeneous mass,
extruding the resulting yeast, so as to obtain
a pressed yeast in the form of fresh yeast cakes or of crumbled fresh yeast, containing approximately 30% of dry matter, or
a yeast in the form of particles, in general of granules, if the yeast is intended to be dried,
optionally, drying in a sparing manner, in a stream of hot air, for example by fluidization, of the yeast particles obtained by extrusion, so as to obtain dry yeast,
packaging.

The drying step is preferably a sparing rapid drying in the presence of an emulsifier.

Among the emulsifiers that can be used during the drying step, sorbitan monostearate, used for example at a concentration of approximately 1.0% (by weight relative to the weight of dry yeast), may be chosen.

The yeasts according to the invention are yeasts which are of reliable quality and which are preferably effective in terms of alcohol production.

The yeasts according to the invention can be used in any possible form.

For example, a subject of the present invention is a yeast as defined above, characterized in that it is in the form of cream yeast, of pressed yeast, of dry yeast or of deep-frozen yeast.

Fresh yeasts are characterized by a high water content in comparison with dry yeasts. Fresh yeasts encompass cream yeasts and pressed yeasts.

Cream yeasts, also called "liquid yeasts", are aqueous suspensions of yeast cells having a cream-type viscosity.

The term "cream yeast" is understood to mean a liquid suspension, typically an aqueous suspension, of live yeast cells, said suspension having a dry matter content of at least 12% by mass, generally comprised from approximately 12% to approximately 50% by mass (broad definition of cream yeast).

Preferably, the cream yeast corresponds to the definition in the strict sense, i.e. it has a dry matter content comprised from approximately 12% to approximately 25% by mass, preferably from approximately 14% to approximately 22% by mass.

Among the pressed yeasts, a distinction is made between pressed yeasts as a compact block, also called "yeast cakes", which are characterized by a dry matter content comprised from approximately 26% to approximately 35%, and pressed yeasts as granules, which are characterized by a water content comprised from approximately 21% to approximately 35%.

The dry yeasts are characterized by a dry matter content of greater than approximately 92%.

The deep-frozen yeasts are characterized by a dry matter content comprised from approximately 74% to approximately 80%.

The yeast according to the invention therefore has the characteristics desired for a yeast intended for producing alcohol, namely a reliable quality and an effective alcohol production.

A subject of the present invention is thus also the use of a yeast as defined above, for producing alcohol.

The alcoholic fermentation conditions depend in particular on the type of application desired, for example according to whether it is a brewing, wine-making or distilling fermentation.

The alcoholic fermentation conditions can be readily determined by those skilled in the art.

By way of example, reference may be made to the alcoholic fermentation conditions described in the reference manual "Yeast Technology", $2^{nd}$ edition, 1991, G. Reed and T. W. Nagodawithana, published by Van Nostrand Reinhold, ISBN 0-442-31892-8.

The yeasts according to the invention are particularly advantageous in the following applications:
  "drinking" alcohol, intended for the production of alcoholic beverages, and/or
  industrial alcohol, intended, for example, for biofuels or for chemical industries.

The present invention will now be illustrated by means of the following examples which are given by way of illustration and are in no way limiting.

The examples describe in particular a method for obtaining stable yeast strains according to the invention and the characteristics of said stable yeast strains, and also the characteristics of yeasts obtained from these strains.

EXAMPLE 1

Selection of Stable Yeast Strains and Characteristics Thereof

Materials and Methods
1. Media and Products

The composition of the culture media and the nature of the enzymes used are indicated below.

| Medium 1 | |
|---|---|
| Yeast extract | 3 g |
| Malt extract | 3 g |
| Peptone | 5 g |
| Glucose | 10 g |
| Agar | 20 g |
| pH: 6.2 +/− 0.2 | |
| Water qs 1 L | |
| sterilization: 20 minutes at 121° C. | |

| Medium 2 | |
|---|---|
| Sodium acetate | 6.5 g |
| Agar | 15 g |
| pH: 6.5-7 | |
| Water qs 1 L | |
| sterilization: 20 minutes at 121° C. | |

| Medium 3 | |
|---|---|
| Cane molasses | 5 g |
| $(NH_4)_2HPO_4$ | 500 mg |
| Agar | 30 g |
| pH adjusted to 5.2-5.3 with 10% $H_2SO_4$ | |
| Water qs 1 L | |
| sterilization: 40 minutes at 121° C. | |

| Medium 4 | |
|---|---|
| Sucrose | 100 g |
| Yeast extract | 20 g |
| $MgSO_4$ | 1 g |
| $KH_2PO_4$ | 1 g |
| pH adjusted to 4.7 with lactic acid | |
| Water qs 1L | |
| sterilization: 30 minutes at 121° C. | |

| Medium 5 | |
|---|---|
| Sucrose | 240 g |
| $(NH_4)_2 HPO_4$ | 4.7 g |
| KCl | 0.8 g |
| Tween 80 | 0.5 ml |
| Citrate buffer | 0.2M |
| Vitamin B1 (thiamine) | 4 mg |
| Vitamin B6 (pyridoxine) | 4 mg |
| Nicotinic acid | 40 mg |
| Biotin | 0.01 mg |
| pH: 4.2 | |
| Water qs 1 L | |

| Enzymes: |
|---|
| Zymolyase 100 000 at 20 mg/mL |

Medium 1 is a basic agar culture medium containing the elements required for the growth of the *Saccharomyces cerevisiae* strains according to the invention.

Medium 2 is an agar medium suitable for yeast sporulation.

Medium 3 is an agar culture medium suitable for yeast growth. Medium 3 contains molasses, which is the substrate generally used for the industrial multiplication of yeasts.

Medium 4 is a standard liquid culture medium suitable for yeast multiplication.

Medium 5 is a liquid culture medium suitable for carrying out an alcoholic fermentation.

Zymolyase is an enzyme used after sporulation, in order to partially digest the wall of the asci and to facilitate their dissection.

2. Isolation of Segregants

Step 1: Growth of the Strain on Medium 1

A loop (öse) of the initial strain (stored at −80° C.) is inoculated at the surface of the agar of a Petri dish. The Petri dish is then incubated for 24 hours at 30° C.

Step 2: Sporulation on Medium 2

A loop of the previous culture is inoculated at the surface of the agar of a Petri dish. The Petri dish is incubated for 96 hours at 25° C. The biomass obtained at the surface of the dish is then harvested in 500 μl of sterile water. 25 μl of zymolyase are added to 100 μl of this suspension. The suspension is incubated for 30 minutes at 30° C., before being plated out onto an agar dish of medium 1. Preferably, the dissection of the tetrads is carried out 20 minutes later.

Step 3: Dissection of Tetrads

The tetrads are dissected using a Singer micromanipulator, and then the Petri dish is incubated for 24 hours at 30° C.

Step 4: Storage of Segregants

The segregants are then stored at −80° C. in medium 1 containing 20% glycerol.

3. Successive Subcultures and Number of Generations

Step 1: Growth on Medium 1

A loop of the test strain (stored at −80° C.) is inoculated at the surface of the agar of a Petri dish containing medium 1. The Petri dish is then incubated for 24 hours at 30° C.

Step 2: Successive Subcultures on Medium 3

The test strain is subcultured at the surface of a Petri dish containing medium 3 using the tip of a toothpick. The Petri dish is then incubated for 20 to 24 hours at 30° C.

The following steps are then repeated 11 times:
- subculture of the test strain at the surface of a Petri dish containing medium 3 using the tip of a toothpick,
- incubation of the Petri dish for 20 to 24 hours at 30° C.

Variant of Step 2

Alternatively, the successive subcultures on medium 3 can be carried out according to the following protocol.

The biomass obtained in step 1 is recovered and diluted in distilled water, in order to obtain a suspension of yeasts at 0.5 mg/ml. A Petri dish containing medium 3 is then inoculated at the surface with 100 μl of this suspension.
The Petri dish is incubated for 20 to 24 hours at 30° C.
The following steps are then repeated 11 times:
- the biomass obtained is harvested in 2×2.5 ml of sterile water,
- dilutions are made in order to obtain a suspension of yeasts at 0.5 mg/ml,
- starting from this suspension, a Petri dish containing medium 3 is again inoculated at the surface with 100 μl of said suspension, and
- the Petri dish is incubated for 20-24 hours at 30° C.

Step 3: Calculation of the Number of Generations Obtained in Step 2

Taking $n_g$ to be the number of generations and $X_0$ to be the biomass inoculated, the biomass $X_n$ obtained at the end of n subcultures is given by the following formula:

$$X_n = 2^{n_g} X_o$$

The number of generations is therefore calculated by applying the following formula:

$$n_g = (\log X_t - \log X_0)/\log 2, \text{ i.e. } n_g = 3.3 \log(X_n/X_o)$$

The biomass can be expressed as number of cells or as weight of dry matter.

As regards the number of cells, the yeast cells sampled on the tip of a toothpick or obtained at the end of the incubation on the Petri dish are suspended in 1 ml of water. The number of cells is then obtained by measuring on a flow cytometer.

Approximately 5 generations are obtained between each subculture, which corresponds on average to 60 generations over 12 successive subcultures.

Variant of Step 3

The number of generations obtained at the end of the variant of step 2 is determined in the following way.

The weight of dry matter $(X_o)$ of said yeast suspension is measured, as is the weight of dry matter $(X_t)$ of the yeast suspension harvested after 20 to 24 hours of growth.

The weight of dry matter is measured after dehydration in an oven at approximately 105° C.

The number of generations is calculated by applying the following formula:

$$n_g = 3.3 \log(X_n/X_o)$$

3 to 4 generations are obtained between each subculture, which corresponds to approximately 36 to approximately 48 generations over 12 successive subcultures.

4. Test for Alcoholic Fermentation by Measuring the Ethanol Produced

Step 1: Culture on Medium 1

A loop of the test strain (stored at −80° C.) is inoculated at the surface of a Petri dish containing medium 1. The Petri dish is incubated for 24 hours at 30° C.

Step 2: Preculture in Liquid Medium in a 50 ml Flask

A loop of the previous culture is inoculated into a 50 mL flask containing 20 mL of medium 4. The flask is incubated for 24 hours at 26° C.

Step 3: Culture in Liquid Medium in a 250 ml Flask 6 mL of the culture obtained in the previous step are inoculated into a 250 mL flask containing 150 mL of medium 4. The flask is incubated for 20 hours at 26° C.

The culture obtained is centrifuged at 4500 rpm for 3 minutes, the supernatant is removed and the pellet is resuspended in 100 mL of sterile distilled water (washing). The suspension is again centrifuged at 4500 rpm for 3 minutes and the pellet is resuspended in 20 mL of sterile distilled water.

The weight of dry matter is measured.

Step 4: Alcoholic Fermentation in a 4000 ml Round-Bottomed Flask 1 g of yeast dry matter of the suspension obtained during step 3 is inoculated into a 4000 mL round-bottomed flask containing 1000 mL of medium 5.

The round-bottomed flask is incubated for 72 hours at 35° C. with shaking at 80 rpm.

10 mL of the fermentation must are removed at t=0, t=7 hours, t=24 hours, t=48 hours and t=72 hours.

The fermentation must removed is filtered (0.2μ filter) and the resulting fermentation solution is stored at −20° C.

The concentration of sugar, ethanol and glycerol present in the fermentation solution is then measured by HPLC (HPX87H column).

Results

1. Selection of Segregants

Segregants were isolated from the strains deposited on Sep. 4, 2008 at the CNCM under the numbers I-4071 and I-4072, as indicated in the "Materials and Methods" section.

The sporulation step results in the formation of asci containing 4 haploid spores which are dissected.

Each haploid spore constitutes a segregant.

The segregants stemming from the two strains I-4071 and I-4072 are evaluated in terms of amount of alcohol produced and of stability.

The results for 5 tetrads stemming from the I-4072 strain (numbered from 1 to 5) are given in tables 1.a) to e).

The results for 6 tetrads stemming from the I-4071 strain (numbered from 6 to 11) are given in tables 2.a) to f).

The values given in the tables correspond to the mean obtained over at least three independent tests.

Row (1) indicates the alcohol production of the population R0 of the segregant, expressed as % of that of the population R0 of the I-4072 strain, and therefore provides information on the effectiveness of the segregant.

Row (2) indicates the alcohol production of the population R12 of the segregant, expressed as % of that of the population R0 of said segregant, and therefore provides information on the stability of the segregant.

TABLE 1a)

| Tetrad 1 sign | 1a a | 1b a | 1c α | 1d α |
|---|---|---|---|---|
| (1) | 77 | 97 | 64 | 101 |
| (2) | 103 | 88 | 108 | 77 |

TABLE 2a)

| Tetrad 6 sign | 6a a | 6b a | 6c α | 6d α |
|---|---|---|---|---|
| (1) | 99 | 98 | 56 | 81 |
| (2) | 93 | 94 | 99 | 98 |

TABLE 1b)

| Tetrad 2 sign | 2a a | 2b a | 2c α | 2d α |
|---|---|---|---|---|
| (1) | 100 | 65 | 73 | 100 |
| (2) | 68 | 96 | 101 | 80 |

TABLE 2b)

| Tetrad 7 sign | 7a a | 7b a | 7c α | 7d α |
|---|---|---|---|---|
| (1) | 63 | 97 | 102 | 52 |
| (2) | 103 | 97 | 97 | 154 |

TABLE 1c)

| Tetrad 3 sign | 3a a | 3b a | 3c α | 3d α |
|---|---|---|---|---|
| (1) | 98 | 82 | 97 | 66 |
| (2) | 82 | 100 | 60 | 99 |

TABLE 2c)

| Tetrad 8 sign | 8a a | 8b a | 8c α | 8d α |
|---|---|---|---|---|
| (1) | 53 | 98 | 58 | 100 |
| (2) | 109 | 99 | 100 | 76 |

TABLE 1d)

| Tetrad 4 sign | 4a a | 4b a | 4c α | 4d α |
|---|---|---|---|---|
| (1) | 75 | 94 | 98 | 71 |
| (2) | 98 | 100 | 88 | 100 |

TABLE 2d)

| Tetrad 9 sign | 9a a | 9b a | 9c α | 9d α |
|---|---|---|---|---|
| (1) | 54 | 101 | 101 | 49 |
| (2) | 126 | 95 | 97 | 133 |

TABLE 1e)

| Tetrad 5 sign | 5a a | 5b a | 5c α | 5d α |
|---|---|---|---|---|
| (1) | 99 | 97 | 65 | 68 |
| (2) | 109 | 67 | 121 | 103 |

TABLE 2e)

| Tetrad 10 sign | 10a a | 10b a | 10c α | 10d α |
|---|---|---|---|---|
| (1) | 49 | 96 | 100 | 56 |
| (2) | 104 | 95 | 78 | 107 |

TABLE 2f)

| Tetrad 11 sign | 11a a | 11b a | 11c a | 11d a |
|---|---|---|---|---|
| (1) | 52 | 99 | 52 | 96 |
| (2) | 146 | 88 | 125 | 99 |

The bold characters represent the tetrads which meet the selection criteria applied to the segregants: alcohol production greater than or equal to 90% for row (1) and greater than or equal to 75% for row (2).

2. Crossing and Selection of Hybrids

Among the segregants selected, the α-sign segregants are crossed with the a-sign segregants, so as to obtain hybrids.

The hybrids are then selected on the basis of the following criteria:
stability: the alcohol production of the population Rn is greater than or equal to 97% of that of the population R0, and
effectiveness: the alcohol production of the population R0 is greater than or equal to 95% of that of the population R0 of the I-4072 strain.

Tables 3.a) and 3.b) indicate the results obtained with the hybrids corresponding to the strains according to the invention:
I-4073 and I-4074 strains: hybrids stemming from crossing of segregant 1d with segregant 7b, and
I-4075 strain: hybrid stemming from crossing of segregant 1d with segregant 5a.

The results obtained with the I-4072 strain are also indicated.

Tables 3.a) and 3.b) indicate the results obtained in the test for alcoholic fermentation by measuring the ethanol produced, respectively at 48 h and 72 h.

Column (1) indicates the alcohol production of the population R0 of the strain, expressed as a percentage of that of the population R0 of the I-4072 strain, and therefore provides information on the effectiveness of the strain.

Column (2) indicates the alcohol production of the population R12 of the strain, expressed as a percentage of that of the population R0 of said strain, and therefore provides information on the stability of the strain.

The values given in the tables correspond to the mean obtained over at least three tests.

TABLE 3a)

| Strain | (1) | (2) |
|---|---|---|
| I-4072 | 100.0 | 48.9 |
| I-4073 | 99.9 | 99.1 |
| I-4074 | 100.7 | 98.5 |
| I-4075 | 99.8 | 97.8 |

TABLE 3b)

| Strain | (1) | (2) |
|---|---|---|
| I-4072 | 100.0 | 46.9 |
| I-4073 | 99.7 | 98.3 |
| I-4074 | 99.1 | 99.2 |
| I-4075 | 99.9 | 99.0 |

The hybrids selected are very effective in terms of alcohol production, since the amount of alcohol produced is greater than 99% of that obtained with the I-4072 reference strain (tables 3.a) and 3.b)).

The hybrids also show a very strong stability: the alcohol production between the population R0 and the population R12 decreased by less than 3% for the I-4073, I-4074 and I-4075 hybrids.

In comparison, the alcohol production of the I-4072 strain dropped by more than 50% (tables 3.a) and 3.b)).

To summarize, the results for the population R12 correspond to a yeast having been multiplied over approximately 60 generations, which is greater than or equal to the average number of generations obtained at the end of an industrial yeast multiplication.

EXAMPLE 2

Characteristics of the Yeasts According to the Invention

Materials and Methods
1. Pilot-Scale Production

The I-4073, I-4074 and I-4075 yeast strains are multiplied in 20 liter fermenters, $2^{nd}$ in semi-continuous mode, as described in the reference manual "Yeast Technology", edition, 1991, G. Reed and T. W. Nagodawithana, published by Van Nostrand Reinhold, ISBN 0-442-31892-8.

The yeasts obtained from each strain are then tested in terms of stability, effectiveness and biomass yield.

The evaluation of the stability of the yeasts is carried out according to the stability evaluation test used for the yeast strains, over 12 successive daily subcultures.

The effectiveness is evaluated by measuring the maximum amount of alcohol produced.

The biomass yield is obtained by calculating the mass of yeast produced over the mass of sugar used during the yeast multiplication.

2. Industrial Production

The I-4074 yeast strain is multiplied on the industrial scale.

The evaluation of the stability of the yeasts obtained at the end of the industrial-scale multiplications is carried out according to the stability evaluation test used for the yeast strains, over 12 successive daily subcultures.

The effectiveness is evaluated by measuring the maximum amount of alcohol produced.

Results

The results obtained after pilot-scale multiplications of the yeast strains show that the yeasts stemming from each of the three yeast strains I-4073, I-4074 and I-4075 are stable, and therefore of reliable quality, effective in terms of amount of alcohol produced, and have a good biomass yield.

Furthermore, after industrial multiplication, the yeasts obtained from the I-4074 yeast strain are stable, and therefore of reliable quality. Furthermore, these yeasts are also effective in terms of amount of alcohol produced and have a good biomass yield.

What is claimed:

1. A method for obtaining stable yeast strains, said method comprising the steps of:
crossing an unstable *Saccharomyces* strain being the I-4072 strain with a stable *Saccharomyces* strain selected from the group consisting of the I-4073 strain, the I-4074 strain and the I-4075 strain, so as to obtain at least one hybrid,
wherein the crossing step comprises the following steps:
sporulating said unstable *Saccharomyces* strain and said *Saccharomyces* strain selected from the group consisting of the I-4073 strain, the I-4074 strain and the I-4075 strain, so as to obtain segregants,
culturing said segregants, so as to obtain a population R0 for each segregant,
carrying out m successive subcultures of each segregant, so as to obtain a population Rm of each segregant, m being an integer greater than or equal to 6,
measuring the alcohol production of the population R0 of each segregant, measuring the alcohol production of the population Rm of each segregant and measuring the alcohol production of population R0 of the I-4072 *Saccharomyces* strain,
selecting the segregants for which:
the alcohol production of the population Rm is greater than or equal to 70% of that of the population R0 of said segregant, and
the alcohol production of the population R0 is greater than or equal to 85% of that of a population R0 of the I-4072 *Saccharomyces* strain, so as to obtain effective, stable segregants, and
crossing effective, stable segregants stemming from said unstable strain with effective, stable segregants of opposite sign stemming from said unstable strain or from said other stable strain, so as to obtain at least one hybrid,
culturing said hybrid, so as to obtain a yeast population R0,
carrying out n successive subcultures of the yeast population R0, n being an integer greater than or equal to 6, so as to obtain a yeast population Rn,
measuring the alcohol production of said population R0 and measuring the alcohol production of said population Rn, and
selecting at least one hybrid for which the alcohol production of the population Rn is greater than or equal to 95% of that of the population R0, so as to obtain stable yeast strains,
wherein the unstable yeast strain, being the I-4072 strain, is a strain which, over generations, produces decreasing amounts of alcohol, and
wherein the stable yeast strains are strains for which the alcohol production of the population Rn is greater than or equal to 95% of that of the population R0, wherein the method comprises additional steps of:
measuring the alcohol production of population R0 of the I-4072 *Saccharomyces* strain, and
selecting at least one hybrid for which the alcohol production of the population R0 is greater than or equal to 95% of that of a population R0 of the I-4072 *Saccharomyces* strain.

2. The method according to claim 1, comprising additional steps of
measuring a biomass yield of the I-4072 *Saccharomyces* strain and
selecting at least one hybrid which has a biomass yield greater than or equal to 90% of the biomass yield of the I-4072 *Saccharomyces* strain.

3. The method according to claim 1, comprising an additional step of selecting at least one hybrid which has a biomass yield greater than or equal to 90% of the biomass yield of the I-4072 strain.

* * * * *